United States Patent
Gassiraro

(12) 
(10) Patent No.: US 6,632,845 B1
(45) Date of Patent: Oct. 14, 2003

(54) METHOD FOR IMPROVING MUSCLE CONTROL AND MUSCLE TONE AND IMPROVING SENSORY INTEGRATION

(75) Inventor: Diane M. Gassiraro, 1303 Gerber Woods Dr., Edwardsville, IL (US) 62025

(73) Assignee: Diane M. Gassiraro, Edwardsville, IL (US)

( * ) Notice: Subject to any disclaimer, the term of this patent is extended or adjusted under 35 U.S.C. 154(b) by 1 day.

(21) Appl. No.: 09/684,258

(22) Filed: Oct. 6, 2000

Related U.S. Application Data
(60) Provisional application No. 60/213,925, filed on Jun. 26, 2000.

(51) Int. Cl.$^7$ .......................... A61K 47/32; A61K 31/74
(52) U.S. Cl. .................................. 514/772.5; 424/78.02
(58) Field of Search ...................... 424/78.02; 514/772.5

(56) References Cited

U.S. PATENT DOCUMENTS

| | | | | |
|---|---|---|---|---|
| 4,671,267 A | * | 6/1987 | Stout | 128/156 |
| 5,597,577 A | * | 1/1997 | Mathewson | 424/402 |
| 5,707,635 A | * | 1/1998 | Deckner et al. | 424/401 |

OTHER PUBLICATIONS

Fisher et al., Tactile Defensiveness: Historical Perspectives, New Research A Theory Grows, The American Occupational Therapy Association, vol. 6, No. 2, 1983, pp. 1–4.

Sensory Integration Information, Sensory Integration International/The Ayres Clinic.

Stancliff, Play with a Purpose, Sensory Integration Treatment and Developmental Disabilities, OT Practice, Oct. 1998, pp. 34–36.

Trombly, C. A. et al., Evaluation and Treatment of Somatosensory Sensation, Occupational Therapy for Physical Dysfunction 3rd Edition, pp. 41–53 (1989).

Trombly, C. A., Neurophysiological and Developmental Treatment Approaches, Occupational Therapy for Physical Dysfunction 3rd Edition, pp. 96–160 (1989).

* cited by examiner

*Primary Examiner*—Bennett Celsa

(57) ABSTRACT

A method for improving muscle control, muscle tone, and sensory integration of an individual by applying polyacrylamide gel to the skin overlying the target muscles. A reflex response by the muscles to the temperature of the polyacrylamide gel is desired which improves the individual's control of the muscle, the tone of the individual's muscles, and stimulates the central nervous system positively. Resistance can be optionally applied to the reflex response of the muscles, further reinforcing the treatment and promoting the individual to gain muscle control and improve muscle tone.

10 Claims, No Drawings

METHOD FOR IMPROVING MUSCLE CONTROL AND MUSCLE TONE AND IMPROVING SENSORY INTEGRATION

This application claims priority from U.S. provisional patent application 60/213,925 filed Jun. 26, 2000.

BACKGROUND OF INVENTION

1. Field of the Invention

The present invention generally relates to a method for improving sensory integration related to the central nervous system and muscle tone throughout the body and extremities by applying polyacrylamide gel to the surface of skin that generally overlies target muscle areas. Sensory integration is a neurological process in which a brain organizes sensory information received from one's body or environment for use in bodily movement, body awareness and the body's senses. As polyacrylamide gel is applied to the skin surface, a cooling effect of the gel on the skin stimulates peripheral nerves underlying the skin. The stimulated nerves in turn innervate muscles for a short period of time. The brain organizes the sensory information received from the peripheral nerves resulting in an overall improvement of neuromuscular motor responses of the body.

2. Description of Related Art

Muscle control of individuals can become compromised due to muscle inactivity, cerebral palsy, brain damage, musculature and neural diseases, congenital deformities, injuries to limbs and nerves, head injuries, hypotonia, and autism among other reasons. The lack of muscle control often results in the decrease or loss of muscle tone, which may progress to muscle atrophy and the loss of muscle mass.

The health profession has created several techniques to improve the muscle motor control of patients that suffer from brain damage and other conditions affecting the musculature. These methods focus on a patient's tactile sensation to movement (sensory stimulation), the reflexive response of muscles to tactile stimulation, and the importance of repeating the sensory stimulation procedures for teaching muscle control.

One approach emphasizes controlled sensory stimulation of the muscles by stimulating the overlying skin. These methods are based upon the idea that individuals develop motor patterns from the fundamental reflex patterns present at birth. The motor patterns develop over time as an individual is exposed to sensory stimulation through experiences of life in his or her environment. As the individual responds to the sensory stimulation correctly, the individual learns to increasingly gain more voluntary control over his or her muscles. Thus, an individual suffering from brain damage or other condition effecting muscle control could be treated by applying appropriate sensory stimulation to a sensory receptor similar to what would occur in the normal developmental process in utero. Such sensory stimulation creates a reflex response from the musculature and the patient learns to gain muscle control as the method is repeated. For an individual suffering from a hypotonic muscle condition, the reflex response to sensory stimulation, in addition to gaining muscle control, would also improve the muscle tone and stop the progression of muscle atrophy.

Current theories of treating hypotonic muscles attempt to normalize the tone and control of muscle responses through appropriate controlled sensory stimulation by evoking a reflexive muscle response. The process follows that of the development of an individual. Thus, therapeutic methods are based upon the developmental stage of an individual. The treatment starts at the level of muscle control of the individual and progressively advances the individual to greater and greater control of his or her muscles. As the individual learns to control muscles and muscle groups, the individual can increasingly gain purposeful control of overall body movement and perform activities of daily living. Finally, the current theories stress that repetition of sensory stimulation and the resultant reflexive muscle response is necessary for the individual to learn muscle control.

Tactile Stimulation (Brushing)

One method of sensory stimulation includes quickly brushing the skin with a soft paint brush such as a camel hair brush or a battery operated brush with revolving bristles. The skin that is brushed typically lies immediately over a target muscle or muscle group desired to be stimulated. If a patient lacks muscle control or muscle tone of the back, the sensory stimulation focuses upon the posterior primary rami of the peripheral nerves which innervate the tonic, deep muscles of the back. Thus, brushing the skin overlying the distribution of the posterior primary rami of the peripheral nerves results in the innervation of the back muscles causing increased muscle tone and control. Similarly, the anterior primary rami of the peripheral nerves innervates the superficial muscles. Thus, stimulating the skin over portions of the body innervated by the anterior primary rami improves the muscle tone and control of the superficial muscles of the body.

Similar to improving tone of the back muscles and superficial muscles, the muscle tone and muscle control of the extremities may also be improved using the skin brushing method. The effects of the sensory stimulation to the extremities, however, may often be first observed on the opposite side of the body. Thus, the brushing technique is often conducted on both the extremities which have muscle control and adequate muscle tone as well as the extremities which lack muscle control and are hypotonic.

The brushing stimulation is performed between approximately 5 to 30 seconds for each area where improved muscle tone and control is desired. If no reflexive response is noted after an area is brushed for approximately 30 seconds, the brushing stimulation is repeated from three to five times.

The theory behind the brushing method is that brushing the skin of an individual results in a nonspecific stimulation of the underlying muscles. Once stimulated, the muscles are latent, remaining unresponsive for approximately 30 seconds. After approximately 30 seconds, the muscles co-contract and contraction occurs. The muscles reach their maximum reflexive response varying in time from 30 seconds to approximately 40 minutes after stimulation. The maximum reflexive response time varies based upon the amount of time the muscle desired is to be stimulated, the disorder compromises muscle tone, and muscle control.

Once a patient has gained control of his or her muscles, the brushing technique is discontinued as continued sensory stimulation therapy becomes ineffective for further improvement.

Brushing techniques, however, often do not always provide the reflexive response that is necessary in some cases to promote muscle tone and help a patient gain muscle control. In these instances, a technique using temperature change to provide the necessary sensory stimulation may be used.

Thermal Facilitation (Icing)

Another technique that can be used to stimulate a reflex response of the muscles is thermal facilitation, commonly referred to as "icing." Similar to stimulating the skin with a brush, thermal facilitation or icing involves holding ice on the skin or brushing ice across the skin surface over the area lacking muscle control and/or muscle tone.

Ice, a noxious sensory stimulus, causes a protective reflexive response of an individual's muscles when applied over the sympathetic chain of the nervous system. It can be pressed against the skin for three to five seconds to stimulate postural and muscle tone responses in patients. Ice may also be brushed across the skin surface to elicit reflexive responses of underlying muscles. The skin areas that are targeted are the same as are targeted in the skin brushing techniques, except that the distribution of the posterior primary rami along the back are avoided due to undesired sympathetic nervous system response.

Icing of the extremities has been performed by rubbing the ice across the palms, soles, and dorsal webs of the hands or feet. This creates a reflex response of the extremity muscles. When the muscles contract, physical resistance to the movement by a medical professional is often applied to reinforce the response and help the patient develop voluntary control over the muscles as well as expedite the development of muscle tone.

Icing, however, has a rebound effect that occurs approximately 30 seconds after sensory stimulation treatment with ice is initiated. The rebound effect results from the muscle becoming so stimulated that it becomes temporarily inhibited. Thus, the icing technique is typically applied to the skin surface overlying a target muscle for no more than 30 seconds to avoid the rebound effect and to maximize the usefulness of the muscular reflex response.

In addition to the rebound effect, the icing technique has practical drawbacks for the medical professional practicing the technique on patients. Often, the icing technique is performed at the homes of patients by traveling medical professionals. Thus, the availability of ice becomes an issue since the medical professional's supply melts throughout the day while the medical professional travels between patients' houses. Additionally, while ice creates a noxious response which is desired for eliciting a reflexive muscular response by the patient, the extreme cold is also uncomfortable to the patient. Less noxious substances, such as cold pudding may be substituted for ice. These substitutes, however, have drawbacks of creating a mess for the patients being treated and the medical personnel as well as leaving a sticky residue on patients' skin during treatment. Additionally, food item substitutes have the drawback of having a shorter useful life. Thus, an alternative material to ice and its substitutes is desired which will provide a reflex response, which minimizes patient discomfort, is convenient to use, is easily cleaned up after application on the patient, and possesses a longer useful life.

SUMMARY OF THE INVENTION

Among the objects of the invention, therefore, is the provision of methods for improving muscle control and for treating individuals suffering from hypotonic musculature using polyacrylamide gel. Also provided are techniques in which the stimulatory material, polyacrylamide gel, used in the treatment is readily available, convenient to use by medical professionals, easily cleaned up, and possesses a long useful life.

Briefly, therefore, the present invention is directed to a method for improving muscle control, muscle tone, and sensory integration of individuals lacking muscle control, muscle tone or who experience sensory processing delays.

In the method of the present invention, polyacrylamide gel is applied to the individual's skin which overlays the muscle or muscles lacking muscle control and tone. After a short duration of time, the polyacrylamide gel is removed from the individual's skin.

Resistance optionally may be applied to the reflexive response of extremity muscles after polyacrylamide gel is applied to the individual's skin.

Other objects and features of this invention will be in part apparent to those skilled in the art and in part pointed out in the detailed description provided below.

DETAILED DESCRIPTION OF THE PREFERRED EMBODIMENTS

The present invention relates to a method of treating individuals lacking muscle control, muscle tone, and sensory integration. While prior art treatment methods have used brushes and ice to elicit a reflexive muscle response to sensory stimulation, the present invention uses polyacrylamide gel.

Medical professionals who typically visit patients in their homes, such as occupational and physical therapists, need treatment articles that can be easily prepared, stored, transported, and used as medical visits are made each day.

Polyacrylamide gel is a commercially available polymer that is used for a variety of purposes such as electrophoresis-based biochemical and genetic analytical procedures, decoration, and potting plants. Polyacrylamide gel is prepared by mixing acrylamide copolymer (polyacrylamide crystals) with water. The crystals, when fully hydrated, can hold over 400 times their weight in water. Once prepared, polyacrylamide gel may be kept at room temperature or chilled in a refrigerator, freezer, or cooler. The polyacrylamide gel can then be easily transported in a container throughout the day or for several days without significantly losing its effectiveness or water content.

The treatment method of the present invention uses polyacrylamide gel instead of ice or alternative substances to ice, such as chilled pudding or other food items, to elicit a reflexive response of a patient lacking muscle control and/or muscle tone. Polyacrylamide gel is applied over the skin surface of a patient to produce reflexive responses of underlying muscles. Preferably the polyacrylamide gel is spread across the skin in an amount resulting, in a depth of about one quarter of an inch of polyacrylamide gel on the skin surface. The high water content of the polyacrylamide gel causes an immediate cooling effect to the surface of the skin as the polyacrylamide gel is applied at a temperature that is cooler than an individual's body temperature. A cooling effect also occurs due to evaporation of water from the surface of the polyacrylamide gel that is applied to the skin. While polyacrylamide gel can be effectively used at room temperature, the sensory stimulation of muscles may be amplified by chilling the polyacrylamide gel prior to applying it to an inividual's skin. As the gel causes sensory stimulation of the skin and reflexive reaction of underlying muscles, the patient learns to gain muscle control. Muscle control becomes reinforced as the method is repeated over multiple visits or therapy sessions. The reflex response of muscles to the polyacrylamide gel sensory stimulation also improves the muscle tone and avoids the progression of muscle atrophy of an individual suffering from a hypotonia. After being applied, the polyacrylamide gel is left on the surface of the skin for a short period of time, preferably for approximately 45 seconds, more preferably about 30 seconds, after which the gel is simply and cleanly wiped off the surface of the patient's skin with a towel or cloth.

In addition to improving muscle control and tone, the method also provides sensory integration to individuals with sensory processing delays. The present invention causes an individual's brain to organize sensory information received from his or her body as polyacrylamide gel is applied to the surface of the skin. This enables the individual to interpret his or her environment correctly for appropriate response and behavior in environmental situations.

As polyacrylamide gel can be used at room temperature or at temperatures above freezing, the treatment of the present invention does not have the same level of noxious stimulation as occurs with icing a patient with ice. Thus, the treatment is not as uncomfortable for the patient. Furthermore, the muscles of the patient do not have the same rebound effect of becoming temporarily inhibited after approximately 30 seconds of treatment that occurs when ice is used. Thus, while polyacrylamide gel remains on the skin for 45 seconds or less in the preferred method, the method may still produce effective results without resulting in a rebound effect if the polyacrylamide gel remains on the skin for longer periods of time. It is therefore anticipated that polyacrylamide gel is superior to ice in that patient discomfort is minimized and therapy treatment time can be extended.

Polyacrylamide gel can also be used on the muscles of the extremities. In such a scenario, polyacrylamide gel is applied to skin of the extremity lacking muscle control and/or muscle tone as well as the skin of the opposite extremity if the problem is localized to one side. Once the polyacrylamide gel is applied, resistance may be applied to elicit the reflexive response of the underlying muscle to reinforce the muscle control learning process as well as expedite the improvement in muscle tone. This procedure can also be localized to either the upper or lower extremities, or any muscles of the body. After approximately 45 seconds, more preferably 30 seconds have elapsed, the polyacrylamide gel is removed by wiping it off with a towel, cloth, or the like.

The present invention solves the shortcomings of the prior art. Since polyacrylamide gel does not melt like ice, a medical professional is able to easily transport the polyacrylamide gel from house to house in a container or cooler without the gel losing its effectiveness as patients are treated during the day. The polyacrylamide gel may be prepared in advance of the medical visits by mixing water and polyacrylamide crystals and allowing the crystals to hydrate.

The consistency of the polyacrylamide gel varies from tacky to watery depending on the amount of water retained by the polyacrylamide crystals. The preferable consistency for the treatment of the present invention is one that is slightly tacky such that the polyacrylamide gel can stick to a patient's skin when it is applied while still retaining enough water to produce a cooling effect.

The preparation procedures may vary among the various polyacrylamide gel commercial products, but generally consists of simply mixing water with polyacrylamide crystals (acrylamide copolymer) and allowing the crystals to soak up the water over a period of a couple of hours. The polyacrylamide crystals are allowed to soak up enough water to produce a gel with a desired consistency. Once the desired consistency is attained, excess water may either be poured off, or the hydrated crystals can be placed in a strainer to allow the excess water to drain off of the polyacrylamide gel.

The prepared polyacrylamide gel may then be optionally chilled in a refrigerator, freezer, or cooler. Once prepared, the polyacrylamide gel can be used immediately, stored or transported in a container to the various patients' houses. Storing the polyacrylamide gel in a sealed container slows the evaporation of water from the gel. Thus, a sealed container causes the polyacrylamide gel to retain its desired consistency over a longer period of time than when it is stored in an open container.

Polyacrylamide gel is also superior to using prior art substitutes to ice, such as chilled pudding or other food-based substitutes, as polyacrylamide gel can be cleanly and neatly removed by merely wiping the patient's skin with a cloth or towel. Unlike chilled pudding, polyacrylamide gel leaves no tacky residue on the surface after being wiped off. Furthermore, polyacrylamide gel, unlike chilled food-based substitutes which have limited shelf lives, can be reused simply by allowing the water to evaporate off the gel leaving polyacrylamide crystals (acrylamide copolymer). The crystals can then be stored until a later date when they can again be rehydrated and reused. Alternatively, as the consistency of the polyacrylamide gel becomes increasingly tacky as water retained in the polyacrylamide gel evaporates, water can simply be added to the gel to rehydrate the gel and regain the desired consistency.

In view of the above, it will be seen that the several objects of the invention are achieved.

As various changes could be made in the above methods without departing from the scope of the invention, it is intended that all matter contained in the above description be interpreted as illustrative and not in a limiting sense.

What is claimed is:

1. A method of improving muscle control, muscle tone, and sensory integration of the central nervous system of an individual lacking muscle control, muscle tone, or sensory integration comprising:

Applying polyacrylamide gel on the individual's skin over target muscles,

Maintaining polyacrylamide gel on the skin for a period of time sufficient to elicit a Reflexive response of the target muscles, and Removing polyacrylamide gel from skin.

2. The method of claim 1 wherein the polyacrylamide gel is removed after about 45 seconds or longer.

3. The method of claim 1 wherein the polyacrylamide gel is removed after about 30 seconds.

4. The method of claim 1 wherein the polyacrylamide gel is removed after about 45 seconds.

5. The method of claim 1 wherein the polyacrylamide gel is applied to the skin of extremities.

6. The method of claim 5 further comprising:

applying resistance to the extremities after the polyacrylamide gel is applied.

7. The method of claim 1 wherein the polyacrylamide gel is applied to the skin of upper extremities.

8. The method of claim 1 wherein the polyacrylamide gel is applied to the skin lower extremities.

9. The method of claim 1 wherein the polyacrylamide gel is chilled prior to application to the skin.

10. The method of claim 1 wherein the application and removal of polyacrylamide gel is repeated.

* * * * *